(12) United States Patent
Zhao et al.

(10) Patent No.: US 11,685,866 B2
(45) Date of Patent: Jun. 27, 2023

(54) METHOD FOR THE CONVERSION OF FEEDSTOCK CONTAINING NAPHTHA TO LOW CARBON OLEFINS AND AROMATICS

(71) Applicants: SABIC Global Technologies B.V., Bergen op Zoom (NL); DALIAN INSTITUTE OF CHEMICAL PHYSICS, CHINESE ACADEMY OF SCIENCES, Liaoning (CN)

(72) Inventors: Yinfeng Zhao, Liaoning (CN); Mao Ye, Liaoning (CN); Zhongmin Liu, Liaoning (CN); Hailong Tang, Liaoning (CN); Jing Wang, Liaoning (CN); Jinling Zhang, Liaoning (CN); Tao Zhang, Liaoning (CN); Talal Khaled Al-Shammari, Riyadh (SA)

(73) Assignees: SABIC GLOBAL TECHNOLOGIES B.V., Bergen op Zoom (NL); DALIAN INSTITUTE OF CHEMICAL PHYSICS, CHINESE ACADEMY OF SCIENCES, Liaoning (CN)

(*) Notice: Subject to any disclaimer, the term of this patent is extended or adjusted under 35 U.S.C. 154(b) by 0 days.

(21) Appl. No.: 17/422,679

(22) PCT Filed: Jan. 28, 2019

(86) PCT No.: PCT/IB2019/050689
§ 371 (c)(1),
(2) Date: Jul. 13, 2021

(87) PCT Pub. No.: WO2020/157540
PCT Pub. Date: Aug. 6, 2020

(65) Prior Publication Data
US 2022/0119717 A1 Apr. 21, 2022

(51) Int. Cl.
*C10G 11/18* (2006.01)
*B01J 35/02* (2006.01)
(Continued)

(52) U.S. Cl.
CPC .............. *C10G 11/18* (2013.01); *B01J 35/023* (2013.01); *B01J 35/026* (2013.01); *C07C 4/06* (2013.01);
(Continued)

(58) Field of Classification Search
CPC ............ C10G 11/18; C10G 2300/1044; C10G 2300/301; C10G 2300/4006;
(Continued)

(56) References Cited

U.S. PATENT DOCUMENTS 7,029,571 B1 * 4/2006 Bhattacharyya ....... C10G 11/18
208/77
2008/0156696 A1 7/2008 Niccum et al.
(Continued)

FOREIGN PATENT DOCUMENTS

CN 102286294 A 12/2011
CN 102295510 A 12/2011
(Continued)

OTHER PUBLICATIONS

International Search Report and Written Opinion from PCT/IB2019/050689 dated Nov. 18, 2019, 11 pages.
(Continued)

*Primary Examiner* — Ali Z Fadhel
(74) *Attorney, Agent, or Firm* — Norton Rose Fulbright US LLP

(57) ABSTRACT

Disclosed is a method for producing low carbon olefins and/or aromatics from feedstock comprising naphtha. The method can include the following steps: a) feeding feedstock comprising naphtha into a fast fluidized bed reactor; b)
(Continued)

contacting the feedstock with a catalyst under conditions to produce a gas product and spent catalyst; c) separating the gas product to produce a stream comprising primarily one or more low carbon olefins and/or one or more aromatics; d) transporting the spent catalyst to a regenerator; e) regenerating the spent catalyst in the regenerator to form regenerated catalyst; and f) returning the regenerated catalyst to the fast fluidized bed reactor.

19 Claims, 1 Drawing Sheet

(51) Int. Cl.
| | |
|---|---|
| *C07C 4/06* | (2006.01) |
| *C10G 61/00* | (2006.01) |
| *C10G 69/08* | (2006.01) |
| *C10G 59/00* | (2006.01) |
| *C10G 63/00* | (2006.01) |
| *C10G 35/00* | (2006.01) |
| *C10G 69/10* | (2006.01) |
| *C10G 45/58* | (2006.01) |
| *C07C 4/10* | (2006.01) |
| *C07C 4/12* | (2006.01) |

(52) U.S. Cl.
CPC .............. *C07C 4/10* (2013.01); *C07C 4/12* (2013.01); *C10G 35/00* (2013.01); *C10G 45/58* (2013.01); *C10G 59/00* (2013.01); *C10G 61/00* (2013.01); *C10G 63/00* (2013.01); *C10G 69/08* (2013.01); *C10G 69/10* (2013.01); *C10G 2300/1044* (2013.01); *C10G 2300/301* (2013.01); *C10G 2300/4006* (2013.01); *C10G 2300/4012* (2013.01); *C10G 2300/4018* (2013.01); *C10G 2400/20* (2013.01); *C10G 2400/30* (2013.01)

(58) Field of Classification Search
CPC .... C10G 2300/4012; C10G 2300/4018; C10G 2400/20; C10G 2400/30; C10G 2300/104; C10G 35/00; C10G 45/58; C10G 59/00; C10G 61/00; C10G 63/00; C10G 69/08; C10G 69/10; B01J 35/023; B01J 35/026; C07C 4/06; C07C 4/10; C07C 4/12
See application file for complete search history.

(56) References Cited

U.S. PATENT DOCUMENTS

| | | | |
|---|---|---|---|
| 2009/0012339 A1* | 1/2009 | Choi | C07C 7/04 585/651 |
| 2016/0369189 A1 | 12/2016 | Ward et al. | |
| 2020/0009523 A1* | 1/2020 | Chen | B01J 8/26 |

FOREIGN PATENT DOCUMENTS

| | | |
|---|---|---|
| CN | 102876363 A | 1/2013 |
| CN | 111484387 B | 8/2021 |

OTHER PUBLICATIONS

Wang et al. "Study of cracking FCC naphtha in a secondary riser of the FCC unit for maximum propylene production." Fuel Processing Technology, Elsevier BV, vol. 89, No. 9, Sep. 1, 2008, pp. 864-873.

* cited by examiner

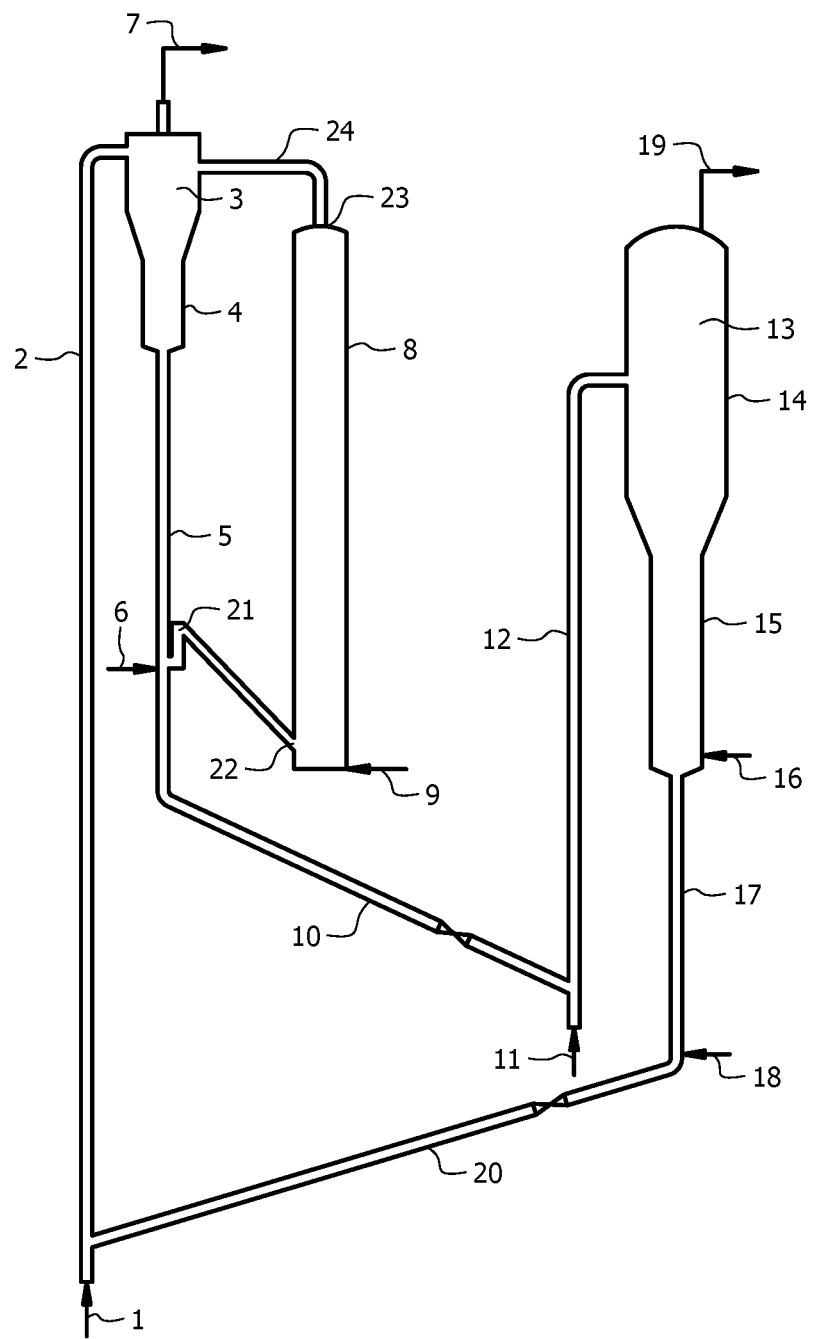

METHOD FOR THE CONVERSION OF FEEDSTOCK CONTAINING NAPHTHA TO LOW CARBON OLEFINS AND AROMATICS

CROSS REFERENCE TO RELATED APPLICATION

This application is a national phase application under 35 U.S.C. § 371 of International Application No. PCT/IB2019/050689 filed Jan. 28, 2019, which is related to PCT Application No. PCT/IB2019/050688, filed Jan. 28, 2019, and entitled, "SYSTEMS FOR CATALYTIC CRACKING OF NAPHTHA WITH MIXED SPENT AND REGENERATED CATALYST," the disclosure of which is incorporated by reference herein in its entirety.

FIELD OF INVENTION

The present application relates to a method for the catalytic conversion of feedstock comprising naphtha to low carbon olefins (light olefins or $C_2$ to $C_4$ olefins) and aromatics.

BACKGROUND OF THE INVENTION

Naphtha is one of the most important raw materials for ethylene and propylene production. High temperature steam cracking of naphtha to produce ethylene and propylene is well-established in the petrochemical industry. Every year, hundreds of million tons of naphtha are used to produce ethylene and propylene, which accounts for more than 50% of the total production of ethylene and propylene. After years of development, steam cracking technology has reached such a high level that its rate of conversion of naphtha to olefins and aromatics is high. But steam cracking has obvious shortcomings. In steam cracking, selectivity is poor, a large amount of methane is generated in the product, the reaction temperature is high, and the energy consumption is high. The potential to develop steam cracking further is small. Therefore, the use of catalytic cracking technology to reduce the cracking temperature has been vigorously pursued. At present, naphtha catalytic cracking technology is mainly carried out in riser reactors to improve the yield of ethylene and propylene. However, naphtha pyrolysis in riser reactors is significant and methane yield is relatively high, both of which are undesirable.

BRIEF SUMMARY OF THE INVENTION

The problems associated with conventional catalytic cracking technology described above can be solved by the technical scheme disclosed in this application. Embodiments of the disclosure include a method for the conversion of feedstock comprising naphtha to low carbon olefins and aromatics. The method can include feeding feedstock comprising naphtha into a fast fluidized bed reactor and contacting the feedstock with a catalyst to obtain a gas product comprising one or more olefins and/or one or more aromatics. The obtained gas product along with spent catalyst, in embodiments of the disclosure, is routed to a stripper, which separates the gas product from the spent catalyst. According to embodiments of the disclosure, the gas product flows through a gas product outlet to a separation system. The separation system separates the gas product to produce a stream comprising low carbon olefins and aromatics. According to embodiments of the disclosure, spent catalyst moves through the stripper, to a stripper inclined pipe, and then a regenerator riser. In the regenerator riser, according to embodiments of the disclosure, the spent catalyst is lifted by gas (e.g., air, nitrogen, carbon dioxide) through the regenerator riser into a regenerator. According to embodiments of the disclosure, the regenerator regenerates the spent catalyst and the regenerated catalyst is then routed to the fast fluidized bed reactor via a stripping section of the regenerator, and a regenerator inclined pipe, and stripper riser. Technical advantages of the method include the reduction of the extent of pyrolysis reaction in naphtha and reduction in the yield of methane in the product as compared with conventional naphtha cracking technology.

Optionally, the catalyst comprises a microsphere catalyst with naphtha catalytic cracking activity and is suitable for a circulating fluidized bed reactor.

Optionally, the reaction conditions of the fast fluidized bed reactor comprise a reaction temperature in a range of 580 to 720° C., a gauge reaction pressure in a range of 0.01 to 0.3 MPa, a gas phase linear velocity in a range of 2 to 10 m/s, and a catalyst to naphtha mass ratio of 10 to 80.

Optionally, the microsphere catalyst is formed by spraying and drying a slurry containing molecular sieve and binder, where the content of the molecular sieve in microsphere catalyst is about 10% to 50 wt. %, and the average diameter is in a range of 30 to 300 μm.

Optionally, the average diameter of the microsphere catalyst is in a range of 50 to 150 μm.

Optionally, the distillation point of the naphtha is in a range of 20 to 200° C.

Optionally, catalyst to naphtha mass ratio is in a range of 20 to 50.

In embodiments of the disclosure, the method for the conversion of feedstock comprising naphtha to low carbon olefins and/or aromatics is characterized by the following steps:

(A) feeding feedstock comprising naphtha into a fast fluidized bed reactor, (B) contacting the feedstock with catalyst, (C) converting the feedstock and catalyst to gas product and spent catalyst, (D) separating the gas product to obtain a stream comprising primarily one or more low carbon olefins and/or one or more aromatics, (E) lifting the spent catalyst by gas into a regenerator, (F) regenerating the spent catalyst to form regenerated catalyst, and (G) transferring the regenerated catalyst to the fast fluidized bed reactor.

Optionally, the one or more low carbon olefins is selected from the list consisting of: ethylene, propylene and butadiene.

Optionally, the one or more aromatics is selected from the list consisting of:

benzene, toluene, and xylene.

Optionally, the reaction conditions in the fast fluidized bed reactor comprise a reaction temperature of 580 to 720° C., gauge reaction pressure in a range of 0.01 to 0.3 MPa, gas phase linear velocity in a range of 2 to 10 m/s, and catalyst to naphtha mass ratio in a range of 10 to 80.

Optionally, the upper limit of the range of reaction temperature for the reaction conditions is chosen from the list consisting of 590° C., 600° C., 610° C., 620° C., 630° C., 640° C., 650° C., 660° C., 670° C., 680° C., 690° C., 700° C., 710° C. and 720° C.; the lower limit of the range of reaction temperature for the reaction conditions is chosen from the list consisting of 580° C., 590° C., 600° C., 610° C., 620° C., 630° C., 640° C., 650° C., 660° C., 670° C., 680° C., 690° C., 700° C., and 710° C., where any of the foregoing upper limit temperatures can be combined with any of the foregoing lower limit temperatures to create a temperature range for the reaction conditions, from a lower value to a higher value.

Optionally, the upper limit of the range of gauge reaction pressure for the reaction conditions is chosen from the list consisting of 0.02 MPa, 0.05 MPa, 0.08 MPa, 0.1 MPa, 0.15 MPa, 0.2 MPa, 0.25 MPa, and 0.3 MPa; the lower limit of the range of gauge reaction pressure for the reaction conditions is chosen from the list consisting of 0.01 MPa, 0.02 MPa, 0.05 MPa, 0.08 MPa, 0.1 MPa, 0.15 MPa, 0.2 MPa, and 0.25 MPa, where any of the foregoing upper limit gauge reaction pressures can be combined with any of the foregoing lower limit gauge reaction pressures to create a gauge reaction pressure range for the reaction conditions, from a lower value to a higher value.

Optionally, the upper limit of the range of gas phase linear velocity for the reaction conditions is chosen from the list consisting of 3 m/s, 4 m/s, 5 m/s, 6 m/s, 7 m/s, 8 m/s, 9 m/s, and 10 m/s; the lower limit of the range of gas phase linear velocity for the reaction conditions is chosen from 2 m/s, 3 m/s, 4 m/s, 5 m/s, 6 m/s, 7 m/s, 8 m/s, and 9 m/s where the foregoing upper limit gas phase linear velocities can be combined with any of the foregoing lower limit gas phase linear velocities to create a gas phase linear velocity range for the reaction conditions, from a lower value to a higher value.

Optionally, the upper limit of the range of the catalyst to naphtha mass ratio is chosen from the list consisting of 20, 30, 40, 50, 60, 70, and 80; the lower limit of the range of the catalyst to naphtha mass ratio is chosen from the list consisting of 10, 20, 30, 40, 50, 60, and 70 where the foregoing upper limit naphtha mass ratios can be combined with any of the foregoing lower limit naphtha mass ratios to create a naphtha mass ratio range for the reaction conditions, from a lower value to a higher value.

Optionally, catalyst to naphtha mass ratio is in a range of 20 to 50.

Optionally, step (E) includes: lifting the spent catalyst by gas into the regenerator via a stripper inclined pipe and a regenerator riser. The gas can include air, nitrogen, and carbon dioxide.

Optionally, step (G) includes: transferring the regenerated catalyst to the fast-fluidized bed reactor via a regenerator stripping section of the regenerator and a regenerator inclined pipe.

Optionally, step (G) includes: transferring the regenerated catalyst to the fast-fluidized bed reactor via the regenerator stripping section, a regenerator inclined pipe, and a stripper.

Optionally, step (G) includes: transferring regenerated catalyst into the fast-fluidized bed reactor via a regenerator stripping section, a regenerator inclined pipe and a stripper for gas solid phase separation.

Optionally, the catalyst comprises a microsphere catalyst with naphtha catalytic cracking activity, where the average diameter of the microsphere catalyst is in a range of 30 to 300 μm.

Optionally, the average diameter of the microsphere catalyst is in a range of 50 to 150 μm.

Optionally, the catalyst comprises a microsphere catalyst comprising a molecular sieve.

Optionally, the weight percentage of the molecular sieve in the microsphere catalyst is 10 to 50 wt. %.

Optionally, the upper limit of the weight percentage of the molecular sieve in the microsphere catalyst is chosen from 20%, 30%, 40%, or 50%; the lower limit is chosen from 10%, 20%, 30%, or 40%.

Optionally, the catalyst comprises a microsphere catalyst comprising molecular sieve ZSM-5.

Optionally, the forming of the microsphere catalyst includes: spraying and drying the slurry containing molecular sieve and binder.

Optionally, the distillation point of the naphtha is in the range 20 to 200° C.

Optionally, the yield of low carbon olefins is 38 to 47 wt. %, the yield of aromatics is 15 to 20 wt. % and the yield of methane is 7 wt. % to 8 wt. % in the gas product.

The beneficial effects of embodiments of the invention include:

1) The volume content in a fast fluidized bed reactor, according to embodiments of the invention is higher than the volume content in a conventional riser reactor, which improves the effectiveness of catalyst and reduces the influence of pyrolysis reaction in embodiments of the invention as compared to conventional naphtha cracking processes.
2) The yield of low carbon olefins can reach 47 wt. %, the yield of aromatics can reach 20 wt. % and the yield of methane can be reduced to 7 wt. % in the product, in the naphtha conversion process, according to embodiments of the invention.
3) There is a reduction in the extent of pyrolysis reaction in naphtha catalytic cracking, which reduces the yield of methane in the product and improves the utilization of carbon atom, in methods according to embodiments of the invention.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

The term "connected" is defined as coupled, although not necessarily directly, and not necessarily mechanically; two items that are "connected" may be unitary with each other.

The term "fast fluidized bed reactor" is defined as a fluidized bed reactor that the catalyst is Geldart A particle[1] and the operation gas line velocity is between 2 and 10 m/s; and where there is a "dense phase region" and a "dilute phase region" in the reactor.

[1] See Deldart D. Types of fluidization, Powder Technology, 1973, 7: 285-290.

The term "dense phase region" is defined as the region that the volume fraction of catalyst more than 0.1 in the reactor; the volume fraction is the value of volume of catalyst in a certain region in the reactor divided by volume of the certain region in the reactor.

The term "dilute phase region" is defined as the region that the volume fraction of catalyst less than 0.1 in the reactor.

BRIEF DESCRIPTION OF THE DRAWINGS

FIG. 1 is a diagram of a system, according to embodiments of the invention. The labels in FIG. 1 have the following meanings: 1: stripper riser inlet, 2: stripper riser, 3: stripper, 4: stripper settling section, 5: stripper stripping section, 6: stripper inlet, 7: product gas outlet, 8: fast fluidized bed reactor, 9: fast fluidized bed reactor feedstock inlet, 10: stripper inclined pipe, 11: regenerator riser inlet, 12: regenerator riser, 13: regenerator, 14: regenerator settling section, 15: regenerator reaction section, 16: regenerator gas inlet, 17: regenerator stripping section, 18: regenerator stripping section gas inlet, 19: regenerator flue gas pipeline, 20: regenerator inclined pipe, and 21: material valve.

DETAILED DESCRIPTION OF THE INVENTION

FIG. 1 shows a system for implementing a method of producing low carbon olefins and aromatics from feedstock comprising naphtha, according to embodiments of the disclosure. The system for producing low carbon olefins and/or aromatics comprises three main components, namely, fast fluidized bed reactor 8, stripper 3, and regenerator 13. According to embodiments of the disclosure, fast fluidized bed reactor 8 is connected to and in fluid communication with stripper 3 and stripper 3 is connected to and in fluid communication with regenerator 13.

Fast fluidized bed reactor 8 is adapted to contact feedstock comprising naphtha with catalyst. As shown in FIG. 1, in embodiments of the disclosure, fast fluidized bed reactor 8 includes fast fluidized bed reactor feedstock inlet 9, which is adapted to allow feedstock material to be flowed into fast fluidized bed reactor 8. Fast fluidized bed reactor 8 also includes fast fluidized bed reactor catalyst inlet 22, which is adapted to allow fast fluidized bed reactor 8 to receive regenerated catalyst. Fast fluidized bed reactor 8 also includes an outlet 23 for allowing effluent material to leave fast fluidized bed reactor 8. The fluid communication between fast fluidized bed reactor 8 and stripper 3 can be provided by pipe 24.

As shown in FIG. 1, in embodiments of the disclosure, stripper 3 comprises one or more gas-solid separators, stripper settling section 4, and stripper settling section 5. The one or more gas-solid separators, for example, can separate gas product from spent catalyst emanating from fast fluidized bed reactor 8. The gas product can be withdrawn from stripper 3 through product gas outlet 7. Stripper settling section 4 is adapted to collect the spent catalyst from reactor 8 through pipe 22 and regenerated catalyst from regenerator 13 through stripper riser 2, and separate the stripping gas and catalyst from the stripper stripping section 5. For example, the line velocity of spent catalyst and gas can be decreased, the stripping gas can be withdrawn from stripper 3 through product gas outlet 7, the catalyst from stripping section 5 settle down, the spent catalyst and regenerated catalyst settle down in settling section 4 after which it moves to stripper stripping section 5. Stripper stripping section 5, in embodiments of the disclosure, is adapted to remove hydrocarbon material from solids such as spent catalyst, the spent catalyst and regenerated catalyst mix together. The mixture of spent catalyst and regenerated catalyst can be routed to the fast-fluidized bed reactor and the regenerator. In this way, a first portion of the mixed catalyst can be routed to the fast-fluidized bed reactor and a second portion of the mixed catalyst can be routed to the regenerator. Stripper inlet 6 allows gas to be flowed into stripper stripping section 5 to facilitate the removal of hydrocarbons from the spent catalyst. According to embodiments of the disclosure, material valve 21 regulates the movement of partial mixture of spent and regenerated catalyst to fast fluidized bed reactor 8 and/or stripper inclined pipe 10. According to embodiments of the disclosure, stripper inclined pipe 10 provides a connection and fluid communication between stripper stripping section 5 and regenerator riser 12. Thus, partial of mixture of spent and regenerated catalyst can move from stripper stripping section 5 to regenerator riser 12. Configuring stripper inclined pipe 10 to be at an angle less than 90 degrees to the horizontal plane as shown in FIG. 1, according to embodiments of the disclosure, allows movement of the spent catalyst towards regenerator section 13 by gravity.

Regenerator riser gas intake 11 can be located at the bottom of regenerator riser 12 so that gas can be received in regenerator riser 12 and move spent catalyst up regenerator riser 12 and into regenerator 13. Regenerator 13 can include regenerator settling section 14, regenerator reaction section 15, regenerator gas inlet 16, regenerator stripping section 17 and regenerator stripping section gas inlet 18. According to embodiments of the disclosure, regenerator settling section 14 is adapted to settle down the regenerated catalyst from the regenerator reaction section 15. In operation, spent catalyst moves from regenerator settling section 14 to regenerator reaction section 15, where the spent catalyst is contacted with gas that flows through regenerator gas inlet under conditions sufficient to regenerate the spent catalyst and form regenerated catalyst. The regenerated catalyst then moves to regenerator stripping section 17 where the regenerated catalyst can be stripped of hydrocarbons by gas that flows through regenerator stripping section gas inlet 18.

After stripping of the regenerated catalyst, the stripped regenerated catalyst moves to stripper riser 2, where such movement (by gravity) is facilitated by regenerator inclined pipe 20 being at an angle less than 90 degrees to the horizontal plane as shown in FIG. 1. According to embodiments of the disclosure, regenerator inclined pipe 20 is directly in fluid communication with regenerator stripping section 17 and stripper riser 2. Indirectly, regenerator inclined pipe 20 is in fluid communication with regenerator 13 and stripper 3, according to embodiments of the disclosure.

Stripper riser 2 connects and is in fluid communication with regenerator inclined pipe 20 and stripper 3, in embodiments of the disclosure. In this way, stripper riser 2 can receive regenerated catalyst from regenerator inclined pipe 20 and the regenerated catalyst can be moved up stripper riser 2 and into stripper 3 by the flow of gas received through stripper riser inlet 1.

As noted above, the system of FIG. 1 can be used to implement a method of producing low carbon olefins and aromatics from feedstock comprising naphtha, according to embodiments of the invention. The method can include flowing raw material (feedstock) that includes naphtha into fast fluidized bed reactor 8 through fast fluidized bed reactor feedstock inlet 9 so that the naphtha of the raw material contacts catalyst of a fluidized bed that is present in fast fluidized bed reactor 8. In embodiments of the disclosure, the reaction conditions in fast fluidized bed reactor 8 are such that the contacting of the naphtha with the catalyst generates a gas product comprising one or more olefins and/or one or more aromatics and spent catalyst. According to embodiments of the disclosure, the reaction conditions of the fast fluidized bed reactor include: reaction temperature of 580 to 720° C., gauge reaction pressure of 0.01 to 0.3 MPa, gas phase linear velocity of 2 to 10 m/s, and a catalyst to naphtha oil mass ratio of 10 to 80. Optionally, the catalyst to naphtha mass ratio is 20 to 50.

In embodiments of the disclosure, a mixture of the gas product and the spent catalyst is flowed from fast fluidized bed reactor 8 to stripper 3. According to embodiments of the disclosure, stripper 3 is adapted to separate solid from gas and separates the gas product from the spent catalyst. The separated gas product is flowed from stripper 3 through outlet pipeline 7 and the spent catalyst moves to stripper settling section 4, according to embodiments of the disclosure. The product gas can flow from product gas outlet pipeline 7 to a separation system (not shown) that can separate the product gas into a stream comprising primarily low-carbon olefins and aromatics. Stripper settling section 4, in embodiments of the disclosure, collects the catalysts from reactor 8, regenerator 13 and stripper stripping section 5 and the spent catalyst moves from regenerator settling section 4 to stripping section 5.

The spent catalyst is routed to regenerator 13 via stripper inclined pipe 10 and riser 12 and into regenerator settling section 14, in embodiments of the disclosure. Gas can be flowed through regenerator riser gas intake 11 to carry the spent catalyst up regenerator riser 12. Regenerator settling section 14 can settle down the regenerated catalyst from the regenerator reaction section 15. From regenerator settling section 14, the spent catalyst can be moved to regenerator reactor section 15. Regenerator reaction section 15 regenerates the spent catalyst, thereby forming regenerated catalyst. In regenerator 13, the spent catalyst moves from settling section 14 to regeneration reaction section 15. An oxidant (e.g., gas or mixture of oxygen and nitrogen, carbon dioxide or other inert gas) is flowed through regenerator intake 16 so that the oxidant contacts the spent catalyst and causes deposited carbon to be reacted and form carbon monoxide or carbon dioxide and thereby regenerate the spent catalyst to regenerated catalyst. Regenerated catalyst is transported from regenerator reaction section 15 to regeneration stripping section 17. In regeneration stripping section 17, the regenerated catalyst is contacted with stripping gas that is supplied through regenerator stripping section inlet 18. The stripping gas (e.g., gas) separates hydrocarbons from the regenerated catalyst in regenerator stripping section 17 so that stripped regenerated catalyst is transported into regenerator inclined pipe 20, then into riser 2, according to embodiments of the disclosure. Gas flow into riser 2 through riser inlet 1 may lift the stripped regenerated catalyst up riser 2 and into stripper 3. In embodiments of the disclosure, regenerator stripping section 17 is in fluid communication with regenerator inclined section 20, which in turn is in fluid communication with riser 2, which in turn is in fluid communication with stripper 3. Stripper 3 separates the stripped regenerated catalyst from the gas that is provided through riser inlet 1.

After gas-solid separation in stripper 3, in embodiments of the disclosure, the stripped regenerated catalyst enters fast fluidized bed reactor 8 through stripper stripping section 5 and material valve 21.

EXAMPLES

The present application is described in detail below in connection with embodiments, but this application is not limited to these embodiments. If not specified, the raw materials in the application are purchased through commercial channels. In the embodiment, the catalyst is a "sphere containing naphtha catalytic cracking activity," which is prepared according to the method of patent CN200710118286.3. The analysis method in the implementation of this application is as follows: The products were analyzed by Agilent gas chromatography. Conversion and selectivity (olefin yield, aromatics yield and methane yield) were calculated on the basis of mass as follows: Olefin yield=(olefin mass content in product*product mass flow rate)/(product mass flow rate+coke generation rate); aromatics yield=(aromatics mass content in product*product mass flow rate)/(product mass flow rate+coke generation rate); methane yield=(methane mass content in product*product mass flow rate)/(product mass flow rate+coke generation rate) coke rate).

Example 1

In the systems shown in FIG. 1, the catalyst was a microsphere catalyst with naphtha catalytic cracking activity. The weight content of molecular sieve in the catalyst was 30%, and the particle size range was 30-300 microns. The naphtha feed was fed into the fast fluidized bed reactor through the feed port of the fast fluidized bed reactor and contacted the catalyst. The product was fed into the gas outlet pipeline. The catalyst entered the stripper and entered into the regenerator, after stripping, via stripper inclined pipe and riser. Regenerated catalyst entered into the fast fluidized bed reactor via a regenerator stripper and an inclined pipe. Gas product entered into separation system through gas product outlet and pipe to obtain different product. Catalyst circulating amount was controlled by plug valve or slide valve. The composition of the naphtha is listed in Table 1. The reaction conditions of the fast fluidized bed reactor were: reaction temperature 580° C., gauge reaction pressure 0.01 MP, gas phase linear velocity 2 m/s, and catalyst to oil ratio of 10. The yield of olefin was 38%, the yield of aromatics was 15%, and the yield of methane was 7%, all measured by online GC analysis of the product.

TABLE 1

The composition of naphtha

| Composition (wt. %) | Naphtha (IBP-150° C.) | Naphtha (IBP-180° C.) |
| --- | --- | --- |
| N-paraffins | 41 | 35 |
| I-paraffins | 24 | 29 |
| Naphthenics | 15 | 28 |
| Aromatics | 14 | 7 |

Example 2

According to the conditions and steps described in Example 1, the catalyst was a microsphere catalyst with naphtha catalytic cracking activity. The weight percentage of the molecular sieve in the microsphere catalyst was 10 wt. %, and the diameter is 50 to 150 μm. The reaction conditions within the fast fluidized bed reactor included: reaction temperature of 650° C., gauge reaction pressure of 0.1 MPa, gas phase linear velocity of 5 m/s, and catalyst to oil ratio of 20. The yield of olefin was 43%, the yield of aromatics was 20%, and the yield of methane was 7%, all measured by online GC analysis of the product.

Example 3

According to the conditions and steps described in Example 1, the catalyst was a microsphere catalyst with naphtha catalytic cracking activity. The weight percentage of the molecular sieve in the microsphere catalyst was 50 wt. %, and the diameter was 50 to 150 μm. The reaction conditions of the fast fluidized bed reactor were: reaction temperature of 690° C., gauge reaction pressure of 0.2 MPa, gas phase linear velocity of 10 m/s, and catalyst to oil ratio of 80. The yield of olefins was 46%, the yield of aromatics was 15%, and the yield of methane was 8%, all measured by online GC analysis of the product.

Example 4

According to the conditions and steps described in Example 1, the catalyst was a microsphere catalyst with naphtha catalytic cracking activity. The weight percentage of the molecular sieve in the microsphere catalyst was 50 wt. %, and the diameter was 50 to 150 μm. The reaction conditions of the fast fluidized bed reactor were: reaction temperature of 690° C., gauge reaction pressure of 0.01 MPa, gas phase linear velocity of 8 m/s, and catalyst to oil ratio of 20. The yield of olefin is 48%, the yield of aromatics was 19%, and the yield of methane is 8%, all measured by online GC analysis of the product.

Example 5

According to the conditions and steps described in Example 1, the catalyst was a microsphere catalyst with naphtha catalytic cracking activity. The weight percentage of the molecular sieve in the microsphere catalyst was 30 wt. %, and the diameter is 50 to 150 μm. The reaction conditions of the fast fluidized bed reactor were: reaction temperature of 720° C., gauge reaction pressure of 0.3 MPa, gas phase linear velocity of 10 m/s, and a catalyst to oil ratio of 50. The yield of olefin was 47%, the yield of aromatics was 15%, and the yield of methane was 8%, all measured by online GC analysis of the product.

As mentioned above, only a few examples of this application do not restrict the application in any form. Although the application is disclosed as above in better embodiments, it is not intended to restrict the application. Any technical personnel familiar with the profession shall make use of the disclosed technology within the scope of the technical scheme of this application. Allowing for a little change or modification is equivalent to the equivalent implementation case, which belongs to the scope of the technical scheme.

What is claimed is:

1. A method of producing low carbon olefins and/or aromatic from feedstock comprising naphtha; the method comprising:
    a) feeding feedstock comprising naphtha into a fast fluidized bed reactor;
    b) contacting the feedstock with a catalyst under reaction conditions in the fast fluidized bed reactor such that the contacting produces a gas product and spent catalyst;
    c) separating the gas product to produce a stream comprising primarily one or more low carbon olefins and/or one or more aromatics;
    d) transporting the spent catalyst to a regenerator;
    e) regenerating the spent catalyst in the regenerator to form regenerated catalyst; and
    f) returning the regenerated catalyst to the fast fluidized bed reactor;
    wherein the catalyst comprises a microsphere catalyst;
    wherein the fast fluidized bed reactor that the catalyst is Geldart A particle and a operation gas line velocity is between 2 and 10 m/s; and where there is a dense phase region and a dilute phase region in the reactor.

2. The method of claim 1, wherein the reaction conditions in the fast fluidized bed reactor comprise:
    a reaction temperature in a range of 580 to 720° C., and
    a reaction pressure in a range of 0.01 to 0.3 MPa.

3. The method of claim 2, wherein the one or more low carbon olefins is a member selected from the group consisting of ethylene, propylene and butadiene.

4. The method of claim 1, wherein the reaction conditions in the fast fluidized bed reactor comprise:
    a catalyst to naphtha mass ratio of 10 to 80.

5. The method of claim 4, wherein the one or more low carbon olefins is a member selected from the group consisting of ethylene, propylene and butadiene.

6. The method of claim 1, wherein the catalyst to naphtha mass ratio is in a range of 20 to 50.

7. The method of claim 1, wherein step f) includes: returning the regenerated catalyst to the fast fluidized bed reactor via a regenerator stripping section and a regenerator inclined pipe.

8. The method of claim 1, wherein the average diameter of the microsphere catalyst is 300 μm.

9. The method of claim 8, wherein the average diameter of the microsphere catalyst is in a range of 30 to 300 μm.

10. The method of claim 8, wherein the average diameter of the microsphere catalyst is in a range of 50 to 150 μm.

11. The method of claim 1, wherein the distillation point of the naphtha is in the range 20 to 200° C.

12. The method of claim 1, further including:
    feeding the feedstock comprising naphtha through an inlet of the fast fluidized bed reactor and into a fast fluidized bed of the fast fluidized bed reactor;
    flowing effluent from the fast fluidized bed reactor to a stripper;

separating, by the stripper, the effluent into the spent catalyst and the gas product;

flowing the gas product into a separation system to obtain a stream comprising one or more low carbon olefins and/or one or more aromatics;

transporting the spent catalyst into the stripper;

transporting the spent catalyst from the fluidized bed reactor through a stripper to a stripper inclined pipe and then to a regenerator riser;

lifting, by gas, the spent catalyst through the regenerator riser into the regenerator; and returning the regenerated catalyst to the fast-fluidized bed reactor via a stripping section of the regenerator and a regenerator inclined pipe.

13. The method of claim 12, wherein the one or more aromatics is selected from the list consisting of: benzene, toluene, and xylene.

14. The method of claim 1, wherein, in the gas product, yield of low carbon olefins is in a range of 38 to 47 wt. %, yield of aromatics is in a range of 15 to 20 wt. % and yield of methane is in a range of 7 wt. % to 8 wt. %.

15. The method of claim 14, wherein the one or more low carbon olefins is a member selected from the group consisting of ethylene, propylene and butadiene.

16. The method of claim 1, wherein the one or more low carbon olefins is a member selected from the group consisting of ethylene, propylene and butadiene.

17. A method of producing low carbon olefins and/or aromatic from feedstock comprising naphtha; the method comprising:
a) feeding feedstock comprising naphtha into a fast fluidized bed reactor;
b) contacting the feedstock with a catalyst under reaction conditions in the fast fluidized bed reactor such that the contacting produces a gas product and spent catalyst;
c) separating the gas product to produce a stream comprising primarily one or more low carbon olefins and/or one or more aromatics;
d) transporting the spent catalyst to a regenerator;
e) regenerating the spent catalyst in the regenerator to form regenerated catalyst; and
f) returning the regenerated catalyst to the fast fluidized bed reactor, wherein step d) includes: transporting the first portion of the spent catalyst from the fluidized bed reactor through a stripper to a stripper inclined pipe and then to a regenerator riser; and
lifting, by gas, the spent catalyst through the regenerator riser into the regenerator;
wherein the fast fluidized bed reactor that the catalyst is Geldart A particle and a operation gas line velocity is between 2 and 10 m/s; and where there is a dense phase region and a dilute phase region in the reactor.

18. The method of claim 17, wherein the one or more low carbon olefins is a member selected from the group consisting of ethylene, propylene and butadiene.

19. A method of producing low carbon olefins and/or aromatic from feedstock comprising naphtha; the method comprising:
a) feeding feedstock comprising naphtha into a fast fluidized bed reactor;
b) contacting the feedstock with a catalyst under reaction conditions in the fast fluidized bed reactor such that the contacting produces a gas product and spent catalyst;
c) separating the gas product to produce a stream comprising primarily one or more low carbon olefins and/or one or more aromatics;
d) transporting the spent catalyst to a regenerator;
e) regenerating the spent catalyst in the regenerator to form regenerated catalyst; and
f) returning the regenerated catalyst to the fast fluidized bed reactor;
wherein in the gas product a yield of low carbon olefins is in a range of 38 to 47 wt. %;
and wherein, in the gas product, yield of aromatics is in a range of 15 to 20 wt. % and yield of methane is in a range of 7 wt. % to 8 wt. %; and
wherein the one or more low carbon olefins is a selection of the list consisting of: ethylene, propylene, and butadiene;
wherein the fast fluidized bed reactor that the catalyst is Geldart A particle and a operation gas line velocity is between 2 and 10 m/s; and where there is a dense phase region and a dilute phase region in the reactor.

* * * * *